US012623030B2

(12) United States Patent
Carrel et al.

(10) Patent No.: US 12,623,030 B2
(45) Date of Patent: May 12, 2026

(54) STANDALONE SAFETY DEVICE FOR A NEEDLE OF A MEDICAL DEVICE

(71) Applicant: Becton Dickinson France, Le Pont de Claix (FR)

(72) Inventors: Franck Carrel, Saint Jean de Vaulx (FR); Olivier Alvain, Seyssins (FR); Gregory Peruzzo, Prunieres (FR)

(73) Assignee: Becton Dickinson France, Le Pont de Claix (FR)

( * ) Notice: Subject to any disclaimer, the term of this patent is extended or adjusted under 35 U.S.C. 154(b) by 719 days.

(21) Appl. No.: 18/011,304

(22) PCT Filed: Jun. 22, 2021

(86) PCT No.: PCT/EP2021/067042
§ 371 (c)(1),
(2) Date: Dec. 19, 2022

(87) PCT Pub. No.: WO2021/259954
PCT Pub. Date: Dec. 30, 2021

(65) Prior Publication Data
US 2023/0233775 A1 Jul. 27, 2023

(30) Foreign Application Priority Data
Jun. 23, 2020 (EP) .................................... 20315316

(51) Int. Cl.
*A61M 5/32* (2006.01)
*A61B 5/15* (2006.01)

(52) U.S. Cl.
CPC ..... *A61M 5/3216* (2013.01); *A61B 5/150664* (2013.01)

(58) Field of Classification Search
CPC .......................... A61M 5/3202; A61M 5/3216
See application file for complete search history.

(56) References Cited

U.S. PATENT DOCUMENTS

2003/0078548 A1* 4/2003 Kobayashi .......... A61M 5/3216
604/263

FOREIGN PATENT DOCUMENTS

| EP | 3302656 B1 | 8/2020 |
| WO | 2016198387 A1 | 12/2016 |
| WO | 2019053112 A1 | 3/2019 |
| WO | 2020254624 A1 | 12/2020 |

* cited by examiner

*Primary Examiner* — Dung T Ulsh
(74) *Attorney, Agent, or Firm* — The Webb Law Firm

(57) ABSTRACT

A standalone safety device for a needle of a medical device A safety device for a needle of a medical device, the safety device including: a ring fixed with regard to the needle, a shield mounted on the ring by a pivot link, a protective cap covering at least partially the needle in an initial configuration, a translation locking unit adapted to prevent a translation movement of the protective cap, and a rotation locking unit adapted to prevent a rotation movement of the shield with regard to the ring. The translation locking unit is configured to be disengaged by the application of a predetermined translation force on the protective cap. The rotation locking unit is configured to be disengaged during a portion of the translation movement of the protective cap with regard to the shield.

13 Claims, 6 Drawing Sheets

7-7'

8-8'

10-10'

11-11'

STANDALONE SAFETY DEVICE FOR A NEEDLE OF A MEDICAL DEVICE

CROSS-REFERENCE TO RELATED APPLICATIONS

This application is the United States national phase of International Application No. PCT/EP2021/067042 filed Jun. 22, 2021, and claims priority to European Patent Application No. 20315316.8 filed Jun. 23, 2020, the disclosures of which are hereby incorporated by reference in their entirety.

BACKGROUND OF THE INVENTION

Field of the Invention

The present invention relates to a standalone safety device for a needle of a medical device, a safety needle hub and a medical device comprising such a safety device.

Description of Related Art

A wide number of medical devices rely on a needle in order to prick a patient's skin and to deliver a medicine or to collect a body fluid. In particular, syringes are a common way of delivering drugs or vaccines to patients and usually comprise an injection needle to deliver such drugs into a patient's skin or a patient's muscle. However, needles present a sharp tip with a risk of needle stick injury, in particular for the medical staff, and it is highly desirable to prevent such needle stick injuries for safety reasons.

Consequently, safety devices have been proposed in order to cover the needle when the needle is not to be used and to allow access to the needle when medical care is performed. For example, document EP3302656 discloses such a safety device with a pivoting shield configured to pivot to an open position when a protective cap is removed from the needle and to cover the needle in a safety position thanks to a simple push on the shield, thus allowing a safe handling and disposal of the syringe after use.

However, the shield of such a prior art safety device is not locked in the initial position and the protective cap is only maintained by friction on the syringe neck. There is thus a risk of unexpected opening of the safety device before use. In addition, such a safety device cannot be assembled before being mounted on a medical device which renders difficult its transportation and mounting to a medical device.

There is thus a need for a safety device overcoming these drawbacks. In other words, there is a need for a safety device preventing any unexpected opening or disassembling and maintaining a high level of protection and sterility of the needle before use. In addition, such a safety device must remain small to limit storage space as well as convenient and safe to use, in particular with gloves and during emergency.

SUMMARY OF THE INVENTION

This objective is accomplished by a safety device for a needle of a medical device, the safety device comprising:
- a ring arranged to be fixed with regard to the needle
- a shield mounted on the ring by a pivot link so as to cover at least partially the needle in an initial configuration of the safety device and to give access to the needle in an operating configuration of the safety device
- a protective cap configured to cover at least partially the needle in the initial configuration

- a translation locking unit adapted to engage the protective cap and the shield to prevent a translation movement of the protective cap with regard to the ring and the shield, below a predetermined translation force
- a rotation locking unit adapted to further engage the protective cap and the shield to prevent a rotation movement of the shield with regard to the ring wherein:
the translation locking unit is configured to be disengaged by the application of the predetermined translation force on the protective cap, to allow a translation movement of the protective cap with regard to the ring and the shield, and the rotation locking unit is configured to be disengaged during a portion of the translation movement of the protective cap with regard to the shield.

The rotation locking unit may be configured to be locked as long as the translation locking unit is not disengaged. Consequently, the shield may be maintained in a close and/or stationary position, during the portion of the translation movement of the protective cap. A translation movement of the protective cap may thus be required, with a translation force above the predetermined translation force, before the disengagement of the rotation locking unit and a possible rotation movement of the shield with regard to the ring. Preferably, the rotation locking unit and the translation locking unit are different locking units, i.e. without any common structural feature.

Thanks to the translation locking unit, the protective cap cannot be removed from the needle unintentionally. Further, the rotation locking unit also prevents any unintentional rotation of the shield with regard to the needle as long as the translation locking unit is activated or locked. The present safety device can thus be transported and handled safely, even if it is not mounted on a medical device. At the time of operating a medical device provided with such a safety device, it is only required to remove the protective cap from the needle with a translation force above the predetermined force to deactivate both the translation locking unit and the rotation locking unit and to access the needle. The present safety device is thus safe to transport and very convenient to use.

Advantageously, the translation locking unit comprises:
- at least one shield protrusion provided on the shield
- at least one cap protrusion provided on the protective cap and located proximally from the shield protrusion so as to prevent the distal movement of the protective cap in the initial configuration by abutting on the shield protrusion, wherein at least part of one of the protective cap and/or of the shield is deformable under the predetermined translation force so that the cap protrusion can reach a distal side of the shield protrusion.

The predetermined force required to deactivate the translation locking unit may thus be set by the type of material, by the thickness of the shield and/or the protective cap and/or by the specific shape of the cap protrusion and the shield protrusion. Consequently, the predetermined force may be adapted to the specific medical device or to the specific market of the safety device.

In addition, two cap protrusions and two shield protrusions may be provided, for example on both lateral sides of the safety device, which improves the reliability of the translation locking unit. The cap protrusion and the shield protrusion may have a triangular cross-section i.e. sloped distal and/or proximal surfaces, which is easy to manufacture and provides a smooth deactivation.

Advantageously, the rotation locking unit comprises:

at least one projection provided on one of the protective cap and the shield at least one rotation blocking abutment and at least one recess provided on the other of the protective cap and the shield wherein:

in the initial configuration, the projection is configured to face the rotation blocking abutment and during the portion of the translation movement, the projection is configured to reach the at least one recess.

The rotation locking unit may thus be designed as a sliding locking unit, configured to be deactivated by the translation or removal movement of the protective cap. Such a rotation locking unit is simple to manufacture and allows a reliable locking of the shield in the initial configuration of the safety device. Preferably, the rotation locking unit may engage the distal portion or extremity of the shield and of the protective cap, in order to allow a more reliable locking.

Advantageously, the one of the protective cap and the shield further comprises a leg pointing in a transversal direction, the leg comprising the projection. This leg may allow more design freedom for the shape of the shield and/or the protective cap and/or a simpler assembly of the safety device.

Preferably, the projection is provided on the shield, which also contributes to a simpler assembly of the safety device. Two projections and two rotation blocking abutments may be provided for a more reliable rotation locking unit. The rotation blocking abutment may form part of a nook adapted to accommodate the projection in the initial configuration of the safety device, which contributes to maintaining the safety device assembled even before being mounted to a medical device.

Advantageously, the leg is flexible and/or the projection is pointing in another transversal direction, perpendicular to the distal direction and to the transversal direction. This allows a simpler assembly of the shield to the protective cap, for example by a linear movement of the shield toward the cap recess of the protective cap.

Alternatively or in combination, the projection is a distal tong that may extend from a leg or directly from the shield and/or from the protective cap. This allows for a simple manufacturing process of the rotation locking unit.

Advantageously, the protective cap and the shield comprise an opening unit adapted to move the shield from a closed position covering the needle to an open position giving access to the needle, during a subsequent portion of the translation movement of the protective cap. In the open position of the shield and after the protective cap has been removed, the safety device is in an operating configuration, ready to be used for medical care. The opening unit allows to switch the safety device from the initial configuration to the operating configuration by the simple movement of removing the protective cap from the ring and/or from the needle.

Advantageously, the opening unit comprises a cam surface provided on the shield and a pusher provided on the protective cap, the pusher being configured to engage the cam surface during the subsequent portion of the removal movement of the protective cap. This allows for a simple to manufacture and reliable opening unit. The cam surface may be provided on a proximal extremity of the shield. Preferably, two pushers and two cam surfaces are provided, for example on both transversal sides of the safety device.

Advantageously, the shield and the ring comprise a safety unit configured to lock the shield to the ring in a safety configuration of the safety device and in a safety position of the shield, in which the shield is adapted to permanently cover the needle. This allows the safety device to be locked after use in the safety configuration, in which it can be safely disposed and stored before destruction.

Advantageously, the safety unit may comprise at least one moving stop defined on the shield, for example on a proximal portion of the shield, and at least one dead stop defined on the ring. The moving stop may be configured to be on a first side of the dead stop in the initial and operating configurations of the safety device and in the open position of the shield, and to be rotated to a second side of the dead stop in the safety position of the shield and in the safety configuration of the safety device.

For example, the moving stop may abut the dead stop in the safety configuration and/or be blocked by the dead stop in the safety configuration. Further, the dead stop may be placed on a path of the moving stop when the shield is moved from the open position to the safety position (in the safety configuration of the safety device) and the shield and/or the moving stop may be deformable so that the moving stop may reach the second side of the dead stop.

Advantageously, the safety device further comprises a guiding unit configured to provide a sliding engagement between the ring and the protective cap. This guiding unit allows to limit the removal movement of the protective cap to a translation movement. The deactivation of the translation locking unit and the rotation locking unit may thus be more reliable, even in case of emergency and when the user wears gloves. In addition, the opening unit may also rotate the shield reliably.

For example, the guiding unit may comprise a distal protrusion on one of the ring and the protective cap and a longitudinal slot provided on the other of the ring and the protective cap. The distal protrusion may be engaged at least partially in the longitudinal slot as long as the protective cap is not removed from the shield and the needle.

Advantageously, the protective cap comprises a needle cap adapted to receive the needle and the protective cap may comprise a recess or cap recess adapted to receive at least part of the shield in the closed position. The needle cap may fully cover the needle, which allows for a high degree of sterility of the needle before use. Receiving part of the shield in the protective cap allows to reduce or limit the volume or size of the safety device and thus to maintain current transportation and storing practices adapted for usual medical devices that may not be provided with a safety device.

For example, the projection and the cap protrusion or the shield protrusion may be a single element. Preferably, the projection, the cap protrusion and the shield protrusion are three distinct elements which increase the reliability of the safety device.

A second aspect of the present invention is a safety needle hub adapted to be fixed on a medical device such as a syringe, the safety needle hub comprising a needle and a safety device according to the first aspect of the present invention. In addition, the safety needle hub may comprise a luer slip or luer lock adaptor.

A third aspect of the present invention is a medical device adapted to inject and/or remove a fluid from a body, comprising a needle and a safety device according to the first aspect of the present invention or a safety needle hub according to the second aspect of the present invention.

A fourth aspect of the present invention is a safety device for a needle of a medical device, the safety device comprising:

a ring arranged to be fixed with regard to the needle a shield mounted on the ring by a pivot link so as to cover at least partially the needle in an initial configuration of the safety device and to give access to the needle in an operating configuration of the safety device a protective cap configured to cover at least partially the needle in the initial configuration a translation locking unit adapted to engage the protective cap and the shield to prevent a translation movement of the protective cap with regard to the ring and the shield, below a predetermined translation force wherein:

the translation locking unit is configured to be disengaged by the application of the predetermined translation force on the protective cap, to allow a translation movement of the protective cap with regard to the ring and the shield.

A fifth aspect of the present invention is a safety device for a needle of a medical device, the safety device comprising:

a ring arranged to be fixed with regard to the needle a shield mounted on the ring by a pivot link so as to cover at least partially the needle in an initial configuration of the safety device and to give access to the needle in an operating configuration of the safety device a protective cap configured to cover at least partially the needle in the initial configuration a rotation locking unit adapted to engage the protective cap and the shield to prevent a rotation movement of the shield with regard to the ring wherein:

the rotation locking unit is configured to be disengaged during a portion of the translation or removal movement of the protective cap with regard to the shield.

The fourth and the fifth aspect of the present invention may share all the advantageous aspects of the first, second and third aspects of the present invention.

Advantageously, the shield comprises a longitudinal axis parallel to the needle in the closed position, which provides a compact and user-friendly safety needle hub or medical device.

BRIEF DESCRIPTION OF THE DRAWINGS

Further advantages and preferred embodiments of the present invention will become apparent from the following detailed description and drawings, in which.

DESCRIPTION OF THE INVENTION

The present safety device is intended to be used with or on any kind of injection, test or sampling medical device using a needle adapted to prick a patient's body for any kind of prophylactic, diagnosis, aesthetics or therapeutic medical treatment. For example, such a medical device can be a medical syringe or a blood collection tube. The safety device can be provided mounted on the medical device or as a safety needle hub adapted to be fixed on a tip of the medical device. In addition, the safety device can also be provided alone, for example for a subsequent mounting on a syringe or on a medical device, depending on the targeted market or customer.

The safety device according to the present invention is described in the examples of the appended figures as mounted on a syringe as a medical device. As such, in this application, the distal direction must be understood as the direction of injection with reference to the medical device, and the proximal direction is the opposite direction, i.e. the direction toward the hand of the medical caregiver or of the patient.

Description of the First Embodiment

Figure 1:
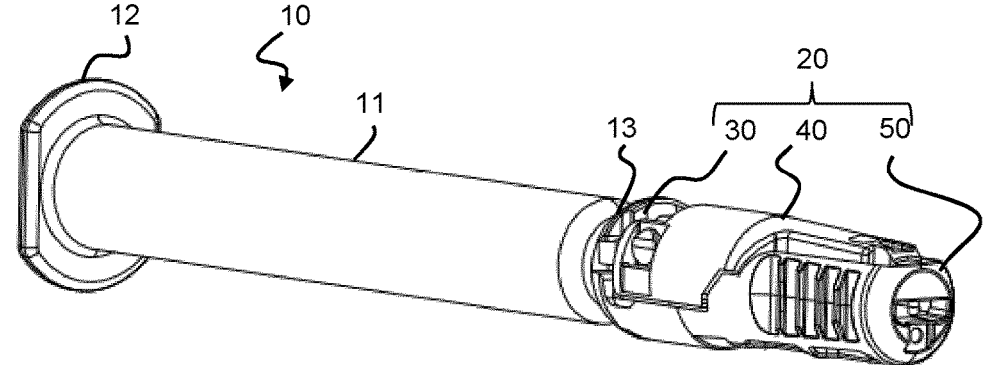
FIG. 1 is a perspective view of the safety device according to a first embodiment of the present invention assembled on a syringe as a medical device.

Referring to FIG. 1, and from proximal to distal or from left to right in the view of FIG. 1, a medical device under the form of a syringe 10 comprises a proximal flange 12, a barrel 11, a distal neck 13 on which a safety device 20 according to the first embodiment of the present invention may be mounted. The safety device 20 comprises a ring 30, a shield 40 and a protective cap 50.

Figure 2:
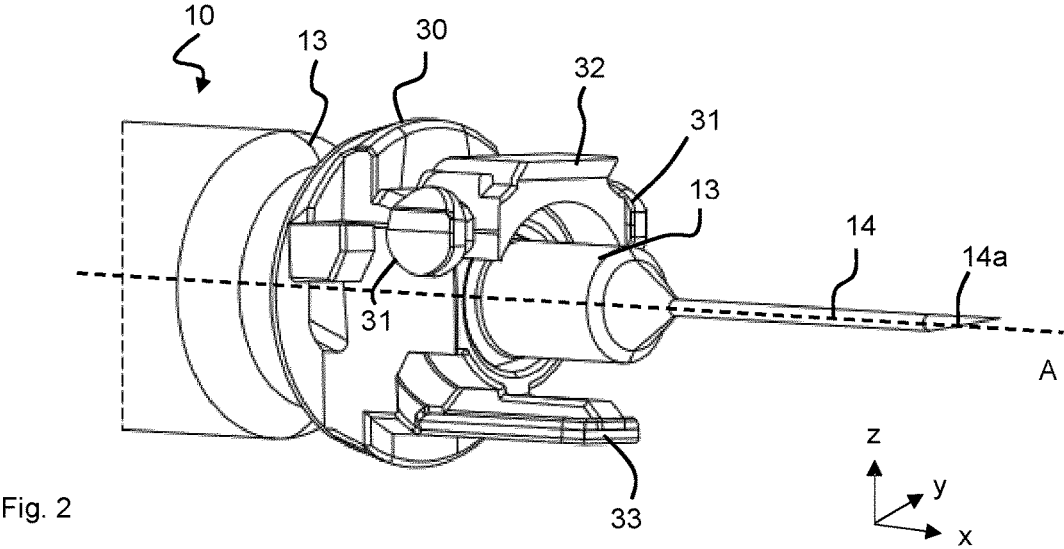
FIG. 2 is a detailed perspective view of a ring of the safety device of FIG. 1.

With reference to FIG. 2, the ring 30 is mounted around the distal neck 13 from which protrudes a needle 14 comprising a tip 14*a*. The ring 30 can comprise two opposite pins 31 adapted to receive part the shield 40 in order to form a pivot link such as a hinge. Further, the ring 30 can comprise a dead stop 32 such as a lug pointing in the distal direction and for example provided with a sloped distal surface and/or extending in between the pins 31. A distal protrusion 33 may also be provided on the ring 30, for example opposite to the dead stop 32. The pins 31 may thus be provided on two lateral and parallel first planes of the ring 30 and the dead stop 32 and the distal protrusion 33 may be provided on two parallel second planes orthogonal to the first planes.

The ring 30 can be centred on a first axis A, such as a revolution axis of the ring 30, and this axis A can be a longitudinal and/or revolution axis of the needle 14 and/or of the syringe 10. For the purpose of this disclosure, the axis A may be considered as an x-axis. The ring 30 is preferably made of hard, rigid material such as a hard polymer or composite adapted for medical use, such as high-density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and their combinations.

Figure 3:
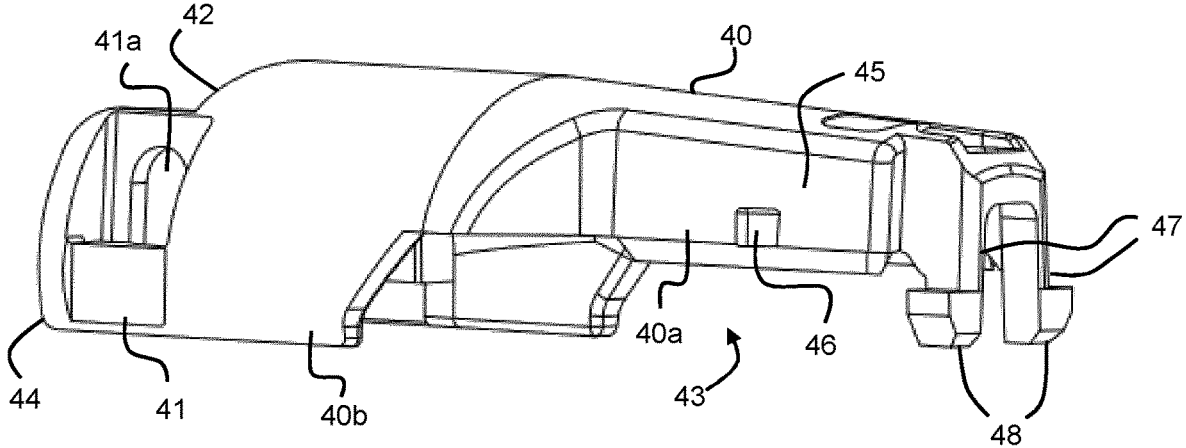
FIG. 3 is a detailed perspective view of a shield of the safety device of FIG. 1.

With reference to FIG. 3, the shield 40 may comprise a hollow body defining a distal part 40*a*, a proximal part 40*b* and a shield recess 43. The proximal part 40*b* may comprise two proximal arms 41 each provided with a lateral opening 41*a* intended to receive a pin 31 of the ring 30. Between the proximal arms 41 is provided a stop surface or moving stop 42 intended to interact with the dead stop 32. Further, each proximal extremity of the proximal arms 41 is provided with a cam surface 44. Opposite the proximal part 40*b* is the distal part 40*a* of the shield 40 defining two lateral surfaces 45, each provided with a shield protrusion 46. For example, the shield protrusions 46 have a triangular cross-section and protrudes laterally, i.e. are orthogonal to the lateral surfaces 45, as visible in FIG. 3.

In the embodiment of FIG. 3, the distal extremity of the shield 40 may comprise two legs 47 each comprising a projection 48. The legs 47 are preferably flexible and may be pointing in a direction transversal to the longitudinal direction of the safety device and the shield, i.e. transversal to the distal direction such as along a third axis or z axis in the first embodiment. Further, the projections 48 may point to another transversal direction, for example orthogonal to the longitudinal direction of the shield and orthogonal to the transversal direction of the legs 47, such as along a second axis or y-axis in FIG. 3 and transversal to the first and third axis.

Figure 4:
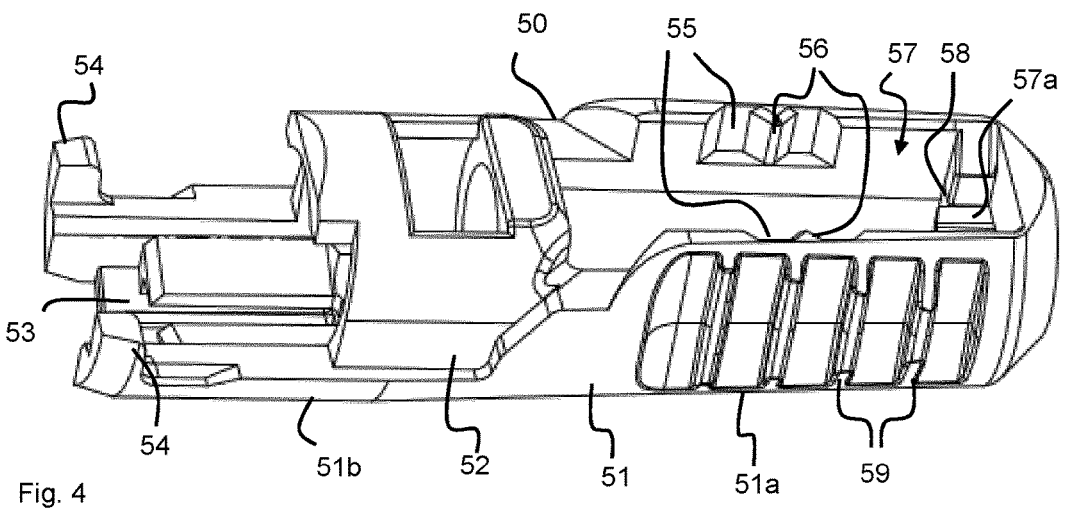
FIG. 4 is a detailed perspective view of a protective cap of the safety device of FIG. 1.
Figure 5:
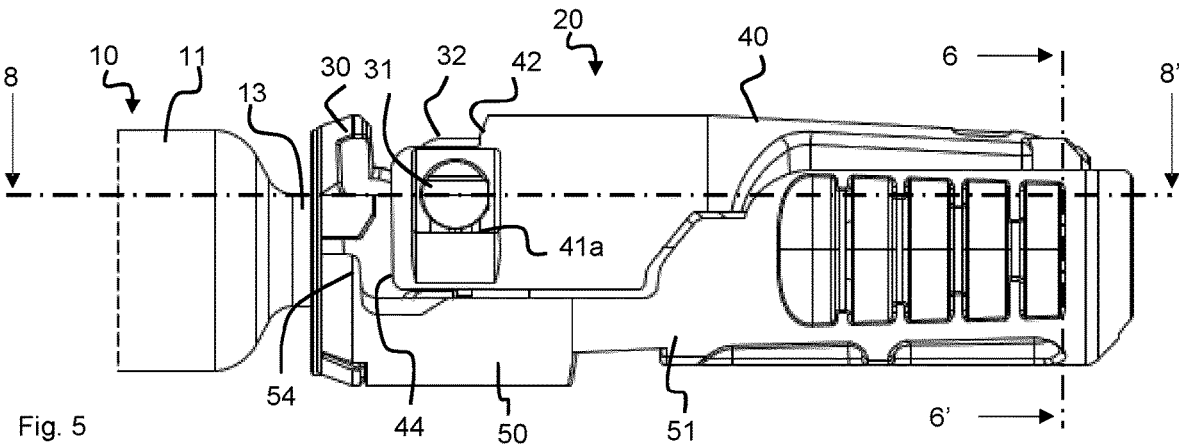
FIG. 5 is a detailed side view of the safety device of FIG. 1, in an initial configuration.

With reference to FIG. 4, the protective cap 50 may comprise a main surface 51 which is substantially U-shaped in the distal portion 51*a* of the protective cap 50 (on the right in FIG. 4) and semi-circular in the proximal portion 51*b* (on the left in FIG. 4). An arch 52 is located between the distal portion 51*a* and the proximal portion 51*b* of the protective cap and may comprise one or several openings in order to fix a needle cap 60 (not shown in FIG. 4), for example by clipping.

The proximal portion 51*b* may comprise a longitudinal slot 53 and two pushers 54 extending for example from its proximal extremity. The longitudinal slot is open proximally and is oriented along the distal direction or the first axis. The distal portion 51*a* of the protective cap 50 further comprises two notches 55 each provided with a cap protrusion 56 facing the inside of the protective cap 50 i.e. the cap recess 57. The distal extremity of the distal portion 51*a* may comprise a distal opening and, nearby the distal opening, two rotation blocking abutments 58 for example on both sides of the distal portion 51*a*. These rotation blocking abutments 58 extend in the cap recess 57 and two nooks 57*a* may be defined between the inside wall of the protective cap 50 and the rotation blocking abutments 58.

The longitudinal slot 53 is configured to accommodate the distal protrusion 33, the cap protrusions 56 are configured to be located proximally from the shield protrusions 46 and the rotation blocking abutments 58 are configured to be engaged by the projection 48, in the initial configuration of the assembled safety device, as detailed below. Finally, the external surface of the distal portion 51*a* may be provided with ridges 59.

The shield 40 and the protective cap 50 may be formed of any polymer adapted to medical use, such as high-density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and their combinations. Preferably, the shield and/or the protective cap may be slightly deformable i.e. have some flexibility.

Figure 6:
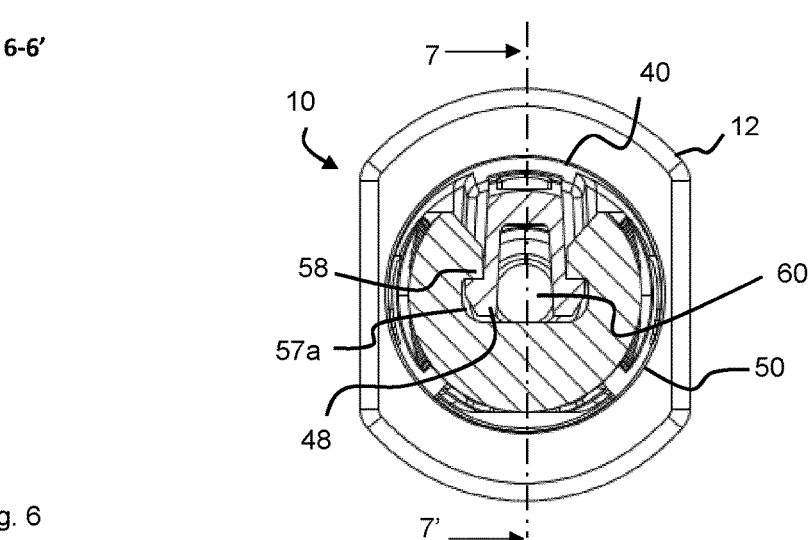
FIG. 6 is a cross-sectional view of the safety device of FIG. 5 along a 6-6' cross-section.
Figure 7:
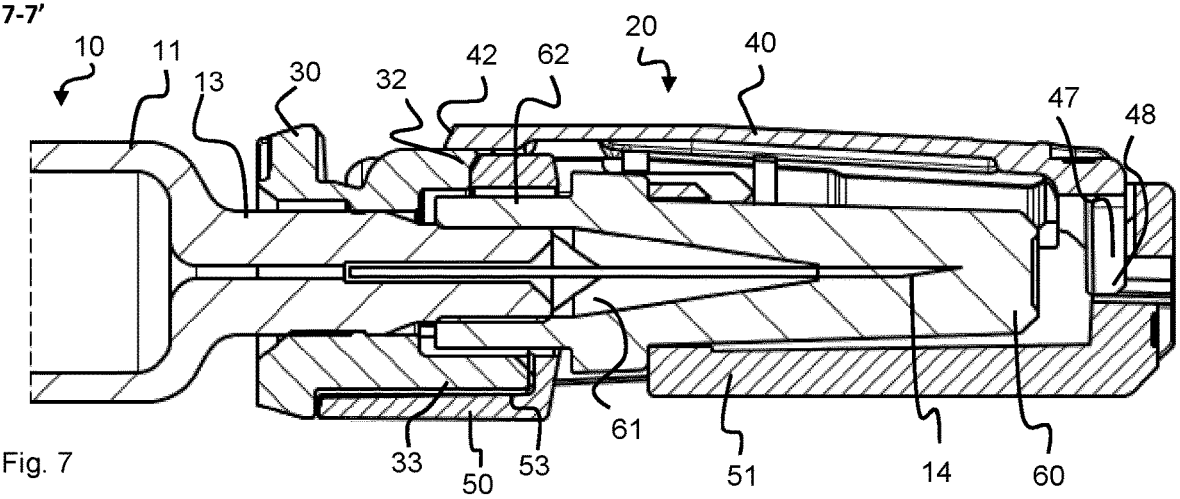
FIG. 7 is a cross-sectional view of the safety device of FIG. 6 along a 7-7' cross-section.
Figure 8:
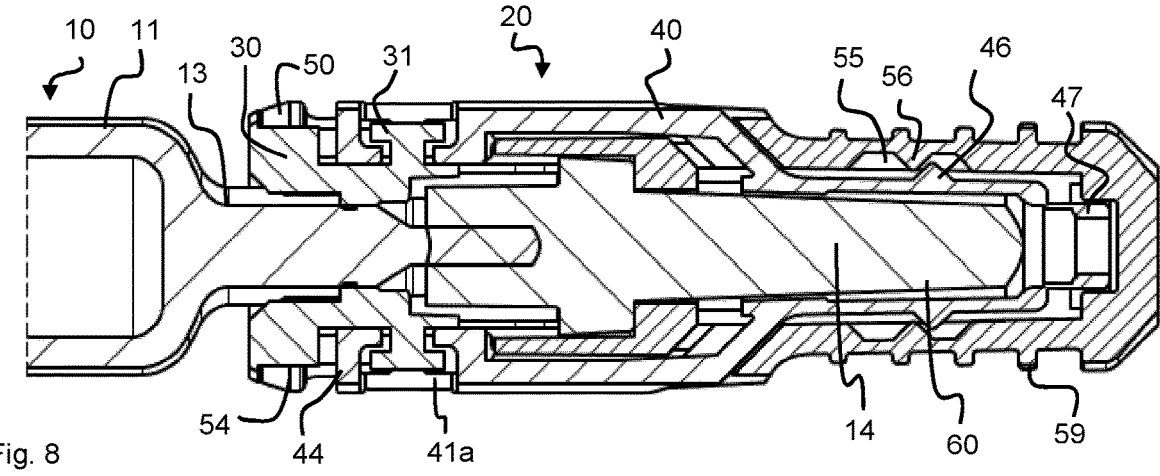
FIG. 8 is a cross-sectional view of the safety device of FIG. 5 along a 8-8' cross-section.

A needle cap 60 (not visible in FIG. 4, see FIGS. 6-8) may be accommodated inside the protective cap 50 and may be clipped, pinched, or maintained by friction with the internal side of the main surface 51 and with the arch 52 of the protective cap 50. The needle cap 60 is thus intended to be fixed with regard to the protective cap 50 and may also be glued to the protective cap 50. Alternatively, the protective cap 50 can be overmolded on the needle cap 60. Preferably, the needle cap 60 is clipped to the arch 52 and/or to a recess or hole of the protective cap 50 opposite the arch 52. The needle cap 60 is intended to accommodate the needle 14 during the storage time of the syringe 10 and thus only comprises a single proximal opening 61 and a proximal edge 62 intended to contact the distal neck 13 in the initial configuration. The needle cap 60 can comprise elastomeric polymer or elastomer such as natural rubber, butyl rubber or silicon rubber.

With reference to FIGS. 5 to 8, the safety device 20 is assembled on the syringe 10 as a medical device and is visible in the initial configuration, similarly to FIGS. 1 and 2. The ring 30 is fixed on the neck 13 of the syringe 10, for example by friction, clipping or gluing. The protective cap 50 is mounted around or on the ring 30 and the distal protrusion 33 of the ring 30 is fitted into the longitudinal slot 53 of the protective cap 50. The needle cap 60 is accommodated in the protective cap 50; it receives part of the needle 14 and may contact the distal neck 13 of the syringe 10 in order to maintain the needle 14 protected from dust and microorganisms.

The shield 40 is mounted in a pivot link on the ring 30 thanks to the pins 31 which are received in the lateral openings 41*a* of the shield 40 and the moving stop 42 of the shield is located on a first side of the dead stop 32 such as a side facing the opening direction of the shield 40. The shield 40 may be partially accommodated in the protective cap 50 and the legs 47 may be inserted into the cap recess 57, between the distal extremity of the needle cap 60 and the distal extremity of the protective cap 50 (see in particular FIG. 6).

In addition, the projections 48 located at the extremities of each leg 47 are located in the nooks 57*a* and abut or at least face the rotation blocking abutments 58: a rotation movement of the shield 40 with regard to the protective cap 50 is thus prevented. The projections 48 and the rotation blocking abutments 58 thus act as a rotation locking unit. In addition, each shield protrusion 46 is accommodated in one of the notches 55, distally from the cap protrusion 56 and a translation movement of the protective cap 50 with regard to the shield 40 and the ring 30 is thus prevented. The shield protrusions 46 and the cap protrusion 56 thus form a translation locking unit.

Operation of the First Embodiment

During storage time, the syringe can be provided into a blister with the safety device in the initial configuration of FIGS. 1 and 5 to 7: the shield 40 is in the closed position, locked to the ring 30 and the protective cap 50 is fixed to the shield 40 and accommodates the needle 14. Thanks to the translation locking unit and the rotation locking unit, the safety device 20 according to the present invention cannot open as a result of shaking, shocks or vibrations that may occur prior to operation of the safety device 20.

Figure 9:
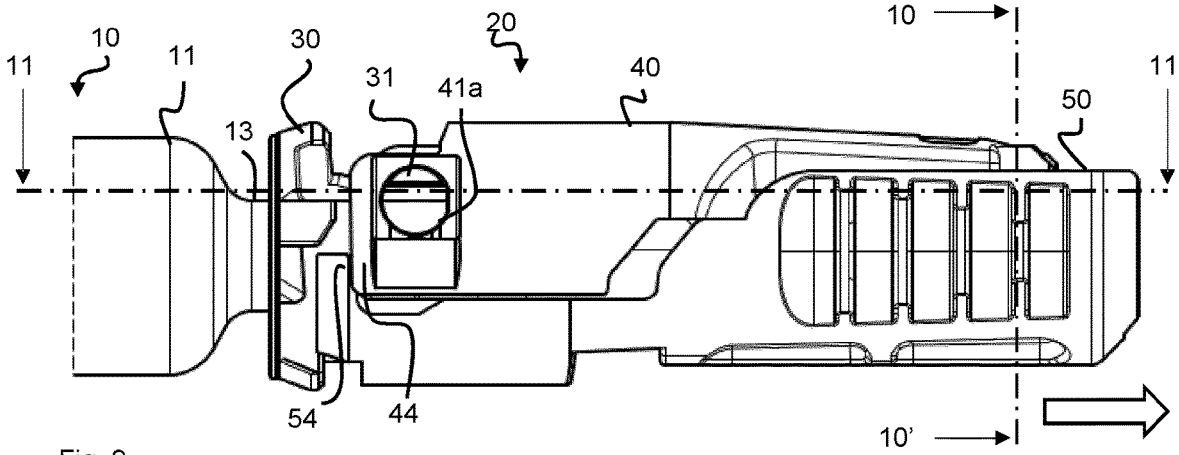
FIG. 9 is a detailed view of the safety device of FIG. 1 after the portion of the removal movement of the protective cap.

At the time of operating the syringe 10 provided with the present safety device 20, a user must first remove the protective cap 50 from the distal neck 13 in order to reveal the needle 14, as usual. To that end, the user can grip the main surface 51 of the cap with his/her fingers, for example on the notches 59, and move the protective cap 50 in the distal direction (on the right of the figures—see the right arrow in FIG. 9).

However, this translation movement is prevented by the translation locking unit since the shield protrusions 46 and the cap protrusions 56 come in contact or abutment, which prevents the translation movement of the protective cap 50. However, the material of the shield 40 and/or of the protective cap 50 allows a limited deformation i.e. has some flexibility. The cap protrusions 56 may thus overcome the shield protrusions 46 and reach the distal side of the notches 55 in a portion of the translation movement of the protective cap 50, when the user pulls the protective cap 50 from the ring 30 with at least a predetermined translation force (see FIGS. 8 and 11). Such a predetermined translation force may be 1 to 5 N, for example 3 N.

Thanks to the preferable engagement between the distal protrusion 33 of the ring 30 and the longitudinal slot 53 of the protective cap 50, only a linear movement in the distal direction of the protective cap is possible and the distal protrusion 33 and the longitudinal slot 53 thus act as a guiding unit establishing a sliding engagement or prismatic joint between the ring 30 and the protective cap 50. The removal movement of the protective cap 50 is thus limited to a linear movement in the distal direction.

Figure 10:
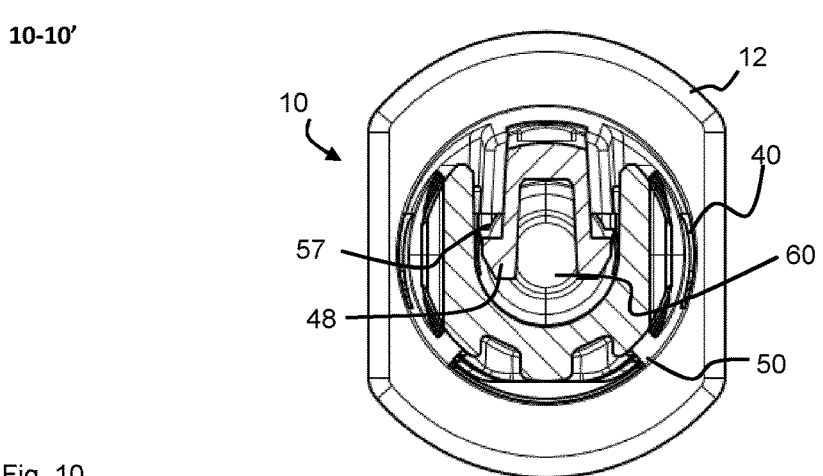
FIG. 10 is a cross-sectional view of the safety device of FIG. 9 along a 10-10' cross-section.
Figure 11:
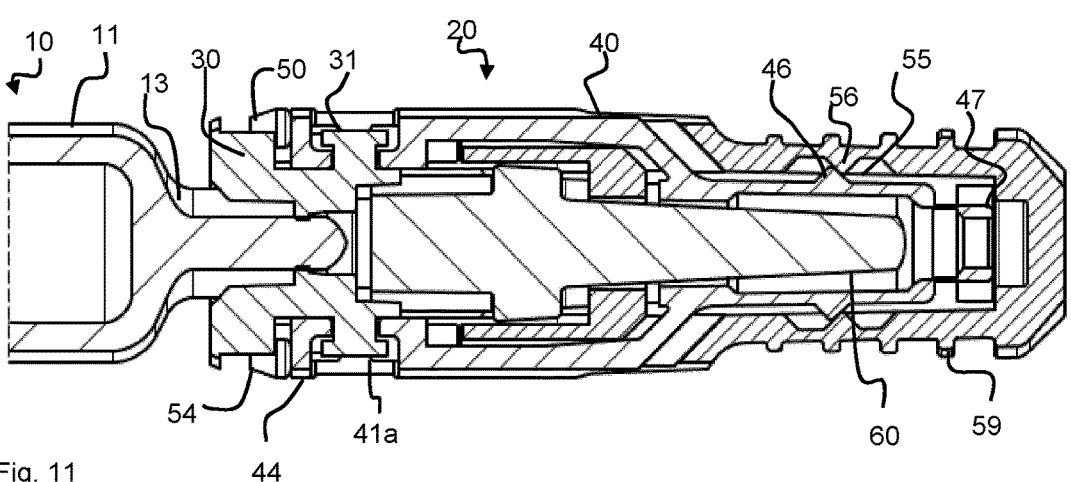
FIG. 11 is a cross-sectional view of the safety device of FIG. 9 along a 11-11' cross-section.

During this portion of the translation movement of the protective cap 50 with regard to the ring 30 and the shield 40 (see FIG. 9, white arrow), the rotation blocking abutment 58 translate with the protective cap 50, so that the projections 48 reaches the cap recess 57 and do not face the rotation blocking abutments 58 anymore (see FIGS. 10 and 11). Consequently, the rotation locking unit is released by a dead run of the protective cap 50 occurring during the release of the translation locking unit. The shield 40 can remain or may be maintained in a still and/or closed position during this dead run.

During the removal movement of the protective cap 50 from the ring 30 and the needle 14, a portion of this movement thus results in the disengagement or release of the translation locking unit and the rotation locking unit. Further, a subsequent portion of this movement results in a rotation of the shield from the closed position to an open position, as detailed below.

Figure 12:
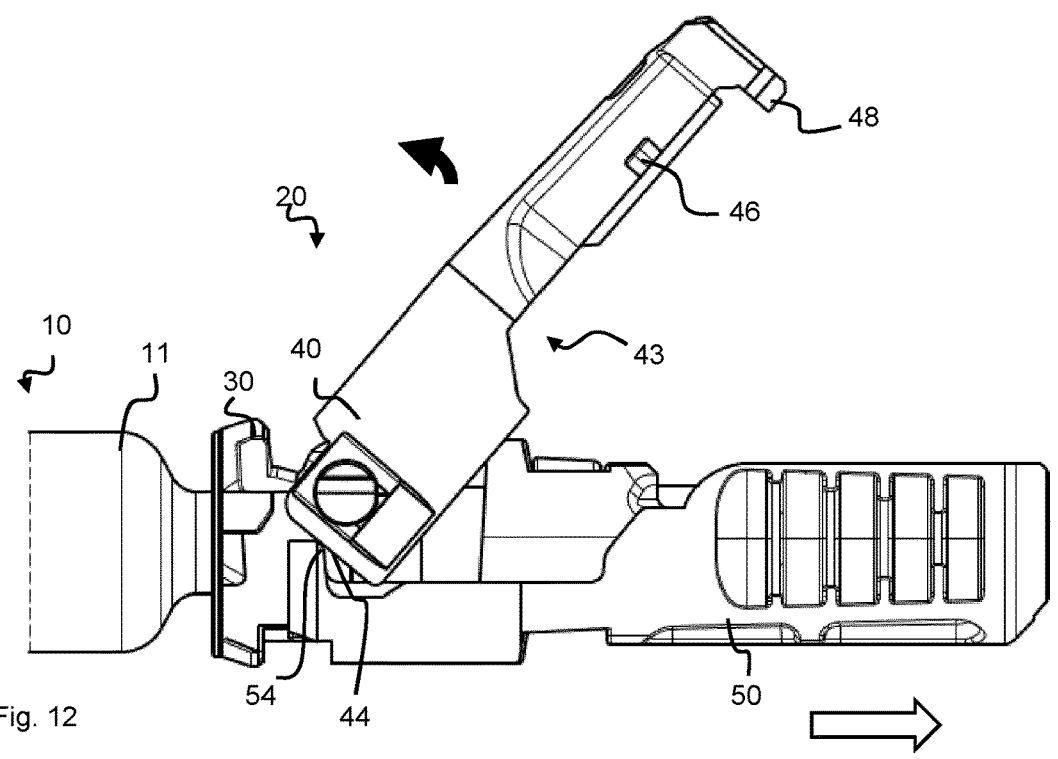
FIG. 12 is a detailed view of the safety device of FIG. 1 in the subsequent portion of the removal movement of the protective cap.

During the portion of the removal movement of the protective cap 50, the pushers 54 move distally and come in contact with the cam surfaces 44. As the removal movement of the protective cap 50 is maintained, the pushers 54 pushes on the cam surfaces 44 which rotates the shield 40 in an opening direction (see the black arrow in FIG. 12) in the subsequent portion of the translation movement. The pushers 54 and the cam surfaces 44 thus acts as an opening unit, adapted to rotate the shield 40 in an opening direction when the protective cap 50 is removed from the ring 30 and the needle 40.

At the end of the subsequent portion of the removal movement of the protective cap 50 (see FIG. 13), the shield 40 may have rotated proximally for example of at least 90° and possibly 120 or 140° with regard to its closed position. The safety device 20 is now in an operating configuration, with the shield 40 in the open position, without the protective cap 50 and with the needle 14 accessible. The needle 14 is thus ready to be used to prick the patient's body and a medicine can be injected thanks to the syringe 10.

Figure 13:
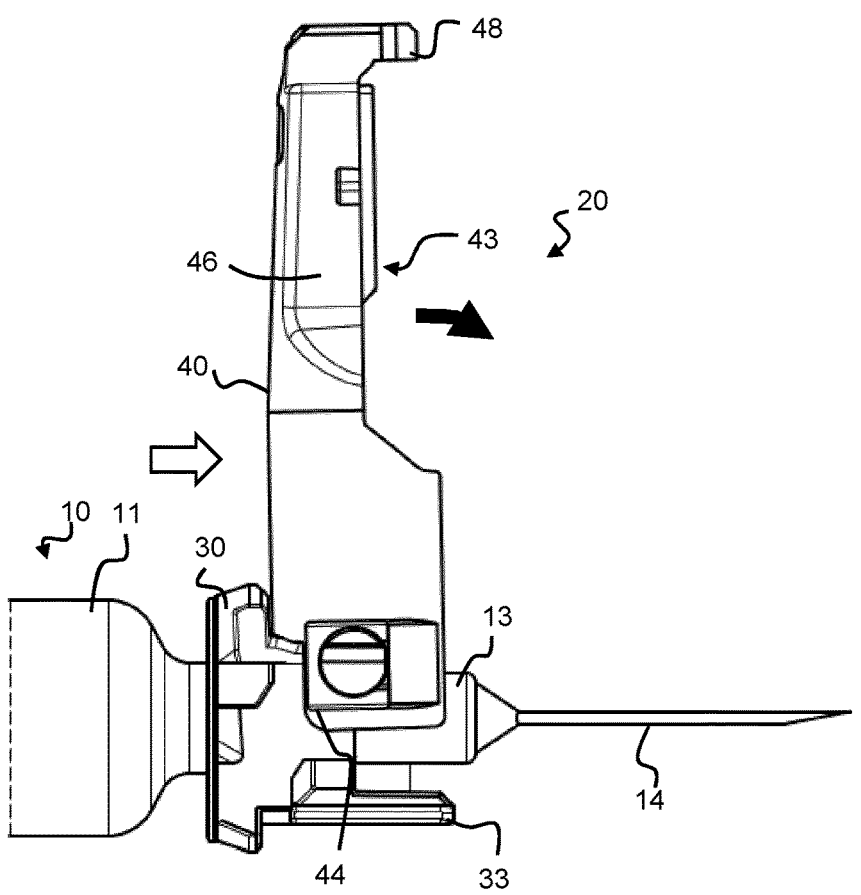
FIG. 13 is a detailed view of the safety device of FIG. 1 in the operating configuration, i.e. after removal of the protective cap, with the shield in the open position.

At the end of the injection operation, the shield 40 can be rotated in a closing direction (see the black arrow of FIG. 13), for example thanks to a force applied by the thumb of the user on the main surface of the shield 40 (see the white arrow in FIG. 13). The dead stop 32 is placed on the path of the moving stop 42 in the closing direction and, according to an operating instruction, an additional force must be applied on the shield 40 so as to deflect the moving stop 42. Such a force may preferably be limited, for example from 1 to 5 N, for example 3 N.

The moving stop 42 can thus reach the second side of the dead stop 32 in an end portion of the closing movement of the shield 40. Consequently, the shield 40 has reached a safety position shown in FIG. 13 and for example form an angle between its longitudinal axis and the revolution axis A of the syringe of around 25° (see FIGS. 5 and 14).

Figure 14:
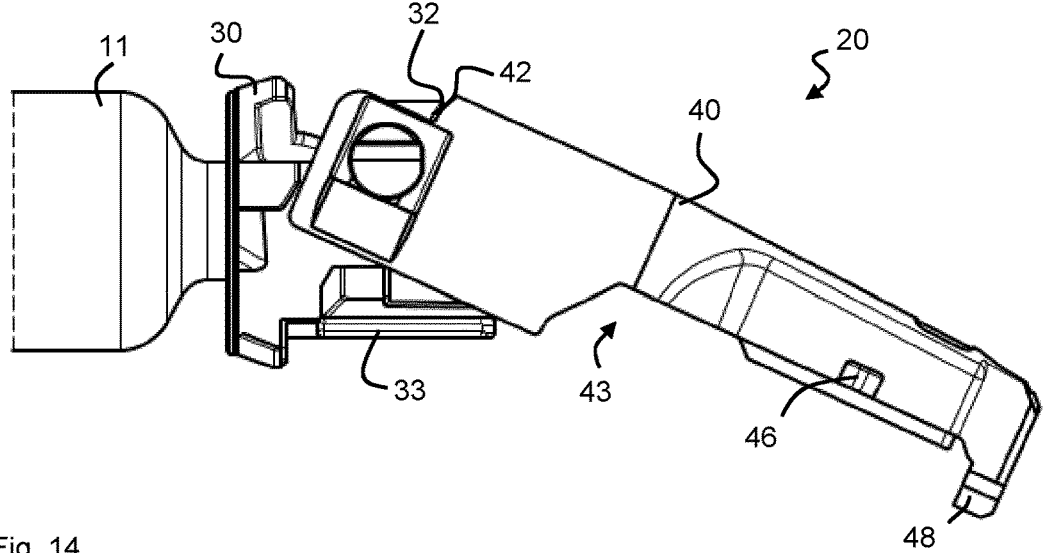
FIG. 14 is a detailed view of the safety device of FIG. 1 in the final, safety configuration.

With reference to FIG. 14, the moving stop 42 is in abutment with the dead stop 32 of the ring 30, on the other side of the dead stop 32, which prevents any movement of the shield and lock the shield 40 to the ring 30. Consequently, the dead stop 32 and the moving stop 42 act as a safety unit to lock the shield 40 in the safety position. In addition, the curved or sloped surfaces of the dead stop 32 and the moving stop 42 may be similar or complementary in order to contribute to the locking engagement.

Further, because of the optional angle made between the shield 40 and the syringe 10, the needle 14 may be bent by the rotation movement of the shield 40 for example on a deflection point, in order to render the syringe 10 visibly improper for use. In addition, a part of the needle 14 can be accommodated in an internal slot of the shield recess 43 of the shield 40. The safety device 20 is thus in a safety configuration and can be safely disposed, with no risk or a limited risk of needle stick injury.

Assembling Process of the First Embodiment

The safety device 20 according to the first embodiment may also be easily assembled by the following process. In a first step, the needle cap 60 may be assembled into the protective cap 50 as usual. In a second step, the protective cap 50 may be positioned or assembled onto the ring 30. In a third step, the shield 40 may be positioned facing the cap recess 57 and parallel to the protective cap 50 i.e. aligned on a longitudinal axis parallel to a longitudinal axis of the protective cap 50. In a fourth step, the shield 40 is approached from the protective cap 50 in a transversal direction, such as along the z-axis, while maintaining the shield 40 parallel to the protective cap 50, such as along the x-axis.

In a fifth step, the shield 40 may contact the ring 30 and the protective cap 50: the proximal arms 41 of the shield 40 may be deflected outwardly so that the pins 31 of the ring 30 may reach the lateral openings 41a. At the same time, the flexible legs 47 may be deflected inwardly so that the projections 48 reaches the location facing the rotation blocking abutment 58, i.e. the nook 57a.

When assembled, the shield 40 is thus fixed to the ring 30 thanks to the engagement of the pin 31 in the lateral openings 41a and fixed to the protective cap 50 thanks the engagement or contact of the projections 48 with the rotation blocking abutments 58. The shield 40 thus allows to assemble the safety device 20 as a standalone safety device before the assembly of the safety device 20 on a medical device. Transport and handling of such a safety device are thus facilitated: for example, the safety device 20 may be produced in one factory and assembled on a medical device in another factory.

Description of the Second Embodiment

Figure 15:
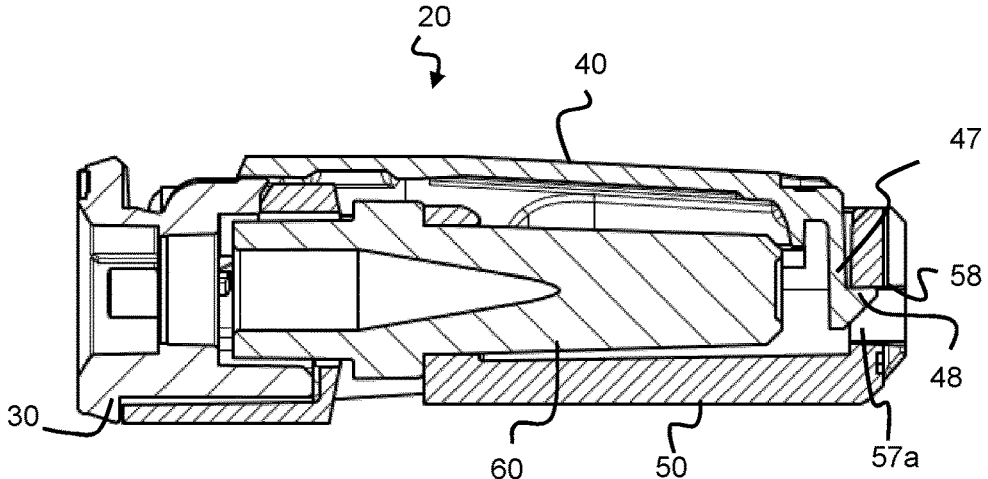
FIG. 15 is a detailed view of a lateral cross-sectional view of a safety device according to a second embodiment of the present invention.

The second embodiment of the present invention is disclosed in FIG. 15 and only differs from the first embodiment described with reference to FIGS. 1 to 14 by the rotation locking unit, all the other features being identical. In FIG. 15, the safety device according to the second embodiment is visible without being mounted on a medical device, i.e. stand alone and in the initial configuration.

The rotation locking unit comprises a leg 47 comprising a projection 48 pointing distally. The leg 47 may be rigid and preferably flexible. The leg 47 may protrude from the distal extremity of the shield 40. The protective cap comprises a cap recess 57 and a rotation blocking abutment 58 adapted to receive the projection 48 i.e. extending distally and not transversally from the cap recess 57 as in the first embodiment. The nook 57a may be provided in the distal direction.

The assembling process of the safety device 20 according to the second embodiment may be similar or identical to the assembly process of the first embodiment.

Description of the Third Embodiment

Figure 16:
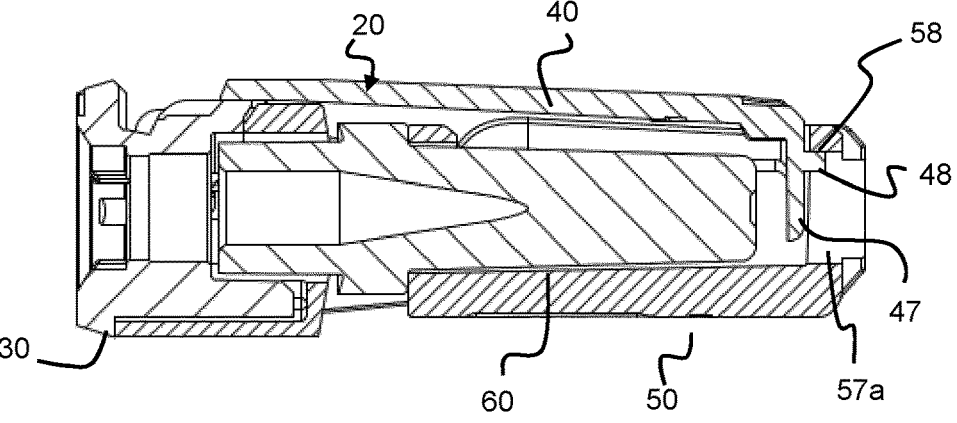
FIG. 16 is a detailed view of a lateral cross-sectional view of a safety device according to a third embodiment of the present invention.

The third embodiment of the present invention is disclosed in FIG. 16 and only differs from the first embodiment described with reference to FIGS. 1 to 14 by the rotation locking unit, all the other features being identical. In FIG. 16, the safety device according to the third embodiment is visible without being mounted on a medical device, i.e. in a standalone and in the initial configuration.

The rotation locking unit comprises a projection 48 pointing distally from the distal extremity of the shield 40. A leg 47 may be optionally provided. The rotation locking unit further comprises a rotation blocking abutment 58 provided at the distal extremity of the protective cap 50 and arranged to face the projection 48 in the initial configuration. The nook 57a may thus be larger than it is in the second embodiment.

The assembling process of the safety device 20 according to the third embodiment may be as follows. In a first step, the needle cap 60 may be first assembled into the protective cap 50 and the protective cap 50 may then be positioned on the ring 30 in a second step. In a third step, the shield 40 may be approached from the protective cap from a position facing the cap recess 57 and with an angle of about 30 to 45°, such as a spoon, in order to engage first the distal extremity of the shield 40 and the leg 47 in the cap recess 57. In a fourth step, the proximal extremity of the shield 40 may then be pushed onto the ring 30 in order for the pin 31 to be received in the lateral opening 41a thanks to an outward deflection of the proximal arms 41 and the projection 48 then faces the rotation blocking abutment 58.

A similar assembly process may also be used in alternatives to the first and second embodiments (not shown) in which the single or the two flexible legs are replaced by a single or two rigid legs.

Although the present invention has been described and illustrated in detail, it is clearly understood that the same is by way of illustration and example only and is not to be taken by way of limitations, the scope of the present invention being limited only by the terms of the appended claims. For example, the elements of the rotation locking unit, the translation locking unit, the guiding unit and the safety unit such as the protrusions, projections, abutments, pushers, etc. may have any shape or geometry as long as their function can be performed.

For example, the translation locking unit may include an adhesive or a frangible tab, in alternative or in combination with the above-described structural features.

Further, the shield protrusions and the cap protrusions of the translation locking unit may be located in other locations of the shield and the protective cap, respectively. For example, the cap protrusion may be located in a bottom portion of the cap recess, or the shield protrusion may extend from the shield in a transversal direction orthogonal to the transversal directions of the shield protrusions 46 of the figures, i.e. along the z-axis.

Similarly, the projection and the rotation blocking abutment of the rotation locking unit are not limited to the distal extremities of the shield and the protective cap, respectively. The moving stop of the safety unit may also be placed in another location of the shield, such as on one or both of the proximal arms. In the safety position of the shield, the shield may not bend the needle but only cover it, for example with a limited angle or even stay parallel to the needle.

The invention claimed is:

1. A safety device for a needle of a medical device, the safety device comprising:
   a ring arranged to be fixed with regard to the needle
   a shield mounted on the ring by a pivot link so as to cover at least partially the needle in an initial configuration of the safety device and to give access to the needle in an operating configuration of the safety device
   a protective cap configured to cover at least partially the needle in the initial configuration
   a translation locking unit adapted to engage the protective cap and the shield to prevent a translation movement of the protective cap with regard to the ring and the shield, below a predetermined translation force
   a rotation locking unit adapted to further engage the protective cap and the shield to prevent a rotation movement of the shield with regard to the ring
   wherein:
   the translation locking unit comprises:
   at least one shield protrusion provided on the shield
   at least one cap protrusion provided on the protective cap and located proximally from the shield protrusion so as to prevent the distal movement of the protective cap in the initial configuration by abutting on the shield protrusion,
   at least part of one of the protective cap and/or of the shield is deformable under the predetermined translation force so that the cap protrusion can reach a distal side of the shield protrusion,
   the translation locking unit is configured to be disengaged by the application of the predetermined translation force on the protective cap, to allow a translation movement of the protective cap with regard to the ring and the shield, and the rotation locking unit is configured to be disengaged during a portion of the translation movement of the protective cap with regard to the shield.

2. The safety device according to claim 1, wherein the rotation locking unit comprises:
   at least one projection provided on one of the protective cap and the shield
   at least one rotation blocking abutment and at least one recess provided on the other of the protective cap and the shield wherein:

in the initial configuration, the projection is configured to face the rotation blocking abutment and during the portion of the translation movement, the projection is configured to reach the at least one recess.

3. The safety device according to claim 2, wherein the one of the protective cap and the shield further comprises a leg pointing in a transversal direction, the leg comprising the projection.

4. The safety device according to claim 3, wherein the leg is flexible and the projection is pointing in another transversal direction, perpendicular to the distal direction and to the transversal direction.

5. The safety device according to claim 2, wherein the projection is a distal tong.

6. The safety device according to claim 1, wherein the protective cap and the shield comprise an opening unit adapted to move the shield from a closed position covering the needle to an open position giving access to the needle, during a subsequent portion of the translation movement of the protective cap.

7. The safety device according to claim 6, wherein the opening unit comprises a cam surface provided on the shield and a pusher provided on the protective cap, the pusher being configured to engage the cam surface during the subsequent portion of the removal movement of the protective cap.

8. The safety device according to claim 1, wherein the shield and the ring comprise a safety unit configured to lock the shield to the ring in a safety configuration of the safety device and in a safety position of the shield, in which the shield is adapted to permanently cover the needle.

9. The safety device according to claim 8, wherein the safety unit comprises at least one dead stop defined on the ring and at least one moving stop defined on a proximal portion of the shield and wherein the moving stop is configured to be on a first side of the dead stop in the open position of the shield and to move to a second side of the dead stop when the shield is rotated to the safety position.

10. The safety device according to claim 1, wherein the safety device further comprises a guiding unit configured to provide a sliding engagement between the ring and the protective cap.

11. The safety device according to claim 1, wherein the protective cap comprises a needle cap adapted to receive the needle, and wherein the protective cap comprises a recess adapted to receive at least part of the shield in the closed position.

12. A safety needle hub adapted to be fixed on a medical device, the safety needle hub comprising a needle and a safety device according to claim 1.

13. A medical device adapted to inject and/or remove a fluid from a body, the medical device comprising a needle and a safety device according to claim 1.

\* \* \* \* \*